United States Patent [19]

Aldrich

[11] Patent Number: 4,600,581

[45] Date of Patent: Jul. 15, 1986

[54] **SYNTHETIC PHEROMONES FOR THE SPINED SOLDIER BUG, *PODISUS MACULIVENTRIS***

[75] Inventor: Jeffrey R. Aldrich, College Park, Md.

[73] Assignee: The United States of America as represented by the Secretary of Agriculture, Washington, D.C.

[21] Appl. No.: 681,394

[22] Filed: Dec. 13, 1984

Related U.S. Application Data

[63] Continuation-in-part of Ser. No. 496,687, May 20, 1983, abandoned.

[51] Int. Cl.[4] .......................................... A01N 25/00
[52] U.S. Cl. ..................................................... 424/84
[58] Field of Search ........................................ 424/84

[56] References Cited

U.S. PATENT DOCUMENTS 4,223,012  9/1980  Anderson et al. ................ 424/84
4,284,622  8/1981  Underhill et al. ................ 424/84

OTHER PUBLICATIONS

Chemical Abstracts, 89: 39687s (1978).
Blum, *Insect Pheremones*, Pesticide Chemistry in the 20th Century, Jack R. Plimmer, ed., USDA, Washington, DC, 1977.

*Primary Examiner*—Albert T. Meyers
*Assistant Examiner*—John M. Kilcoyne
*Attorney, Agent, or Firm*—M. Howard Silverstein; William E. Scott; David G. McConnell

[57] ABSTRACT

A synthetic pheromone formulated from chemicals found in the airborne secretion of *Podisus maculiventris*, the spined soldier bug, was found to be highly effective in attracting *P. maculiventris*, a beneficial predatory insect, to desired areas for biological control of pests.

6 Claims, No Drawings

SYNTHETIC PHEROMONES FOR THE SPINED SOLDIER BUG, PODISUS MACULIVENTRIS

This is a continuation-in-part of application Ser. No. 496,687, filed May 20, 1983, now abandoned.

BACKGROUND OF THE INVENTION

1. Field of The Invention

The invention relates to a synthetic pheromone composition for the spined soldier bug, *Podisus maculiventris*, to its composition and to its uses.

2. Description of The Art

Pheromones have been identified for many arthropod pests. However, with the exception of the silkworm and the honey bee, which are rather special cases in that they are partially domesticated insects, no pheromones of beneficial insects have been chemically identified. In fact, suspected pheromones have been identified for only a few species of Hemiptera and the aggregation pheromone of *P. maculiventris* is the only synthetic pheromone for a member of the order Hemiptera that has been produced and found to be active under natural field conditions.

SUMMARY OF THE INVENTION

An object of this invention is to provide a synthetic pheromone composition for the spined soldier bug, *Podisus maculiventris*.

Another object is to provide a synthetic pheromone for a beneficial predatory insect.

Still another object is to provide a synthetic pheromone which attracts not only the spined soldier bug but also certain of its parasites.

A further object is to provide a means by which the predatory nature of the spined soldier bug can be utilized in pest management.

A still further object is to provide a composition and a means by which the spined soldier bug can be introduced into geographic areas other than those areas in which it has been found heretofore.

Still another further object is to provide a composition and a means of attracting parasitoids of *P. maculiventris* so they can be destroyed.

According to this invention the above objects are accomplished by a composition comprised of an effective attractant mixture of (E)-2-hexenal, α-terpineol, benzyl alcohol, linalool, and terpinen-4-ol and the use of the composition to attract the insect *P. maculiventris* and its parasitoids. Each component in the mixture is present in proportions approximating the proportions that each is found in the natural pheromone of the spined soldier bug, *Podisus maculiventris*.

DESCRIPTION OF THE INVENTION

Pheromones have been identified for hundreds of arthropod pests. The rapid proliferation of pheromone research since the identification of the silkworm's pheromone in 1959 attests to the potential usefulness envisioned for these specific and powerful triggers of behavior. With the exception of the silkworm and the honey bee, which are rather special cases in that they are partially domesticated insects, no pheromones of beneficial insects have been chemically identified. The importance of predators and parasitoids in constraining populations of the species on which they live is amply appreciated by entomologists, yet we have a meager understanding of how these species find their prey or host and their mates. As our awareness of the dangers of environmental contamination with pesticides has increased and as the cost of pesticides has risen, efforts to develop safer and cheaper methods of pest management have intensified. The judicious use of pheromones is contributing to the necessitated refinements of pest management procedures. An important distinction between the use of the pheromones of pests and predators is that pheromonal control of pests usually has a delayed effect dependent on killing or otherwise preventing the adult stage of the pest from reproducing, whereas control programs involving the use of pheromones to augment the predator population in an infested area would have an immediate impact on the pest and would not depend on killing or unnaturally disorienting the individuals attracted. Identification and synthesis of the pheromones of key beneficial species could lead to important advances in biological control. Predators could be attracted to the site of an infestation or, alternatively, they could be attracted out of the infested area prior to pesticide application thereby minimizing future buildup of pests due to destruction of their predators. Using pheromones may make it possible to decrease parasitization of predators, thus augmenting the predator population. The feasibility of mass releasing pathogen contaminated *P. maculiventris* adults to spread disease in crop pests as a means of eliminating or greatly reducing the population of such pests is currently being investigated. The aggregation pheromone described herein would be useful in this context to hold the released predators in the desired area. An exciting and heretofore unexplored use of pheromones is in the establishment of colonies of predators and parasites of pest insects in foreign countries and other geographic areas to which they are not endemic. The predators and parasitoids introduced for this purpose should be released in the immediate locality of the synthetic pheromone to improve their initial reproductive success and insure their propagation.

The spined soldier bug, *Podisus maculiventris*, has been referred to as the most useful of the American predaceous Hemiptera. This insect occurs naturally throughout the U.S. and southern Canada and has been approved for introduction into Europe as a biological control agent. The bug is an active predator of many insects, including several economically important pests.

Adult males of *P. maculiventris* release a volatile secretion which when analyzed by combined gas chromatography-mass spectrometry yielded the following composition, the amount of each component being based on the % area of the peaks of the gas chromatograms of the airborne extracts: 48.5% (E)-2-hexenal, 46.1% (+)-α-terpineol (α,α,4-trimethyl-3-cyclohexene-1-methanol; p-menth-1-en-8-ol), 4.5% benzyl alcohol (benzenemethanol; phenylcarbinol; phenylmethanol; α-hydroxy-toluene), 0.3% linalool (3,7-dimethyl-1,6-octadien-3-ol; 2,6-dimethyl-2,7-octadien-6-ol; linalol), 0.2% terpinen-4-ol (4-methyl-1-(1-methylethyl)-3-cyclohexen-1-ol), and 0.4% cis-piperitol (3-methyl-6-(1-methylethyl)-2-cyclohexen-1-ol; p-menth-1-en-3-ol; 4-isopropyl-1-methyl-1-cyclohexen-3-ol). As noted hereafter, the α-terpineol probably contains a small amount of the antipode, that is, (−)-α-terpineol.

Various methods and materials were employed to isolate the pheromone to identify the components, to synthesize and formulate the active compounds, and to test the behavioral responses to the synthetic pheromone.

A laboratory culture of *P. maculiventris* was maintained on larvae and pupae of *Tenebrio molitor* plus distilled water. The insects were kept at 27° C. on a 16L:8D photoperiodic regime.

Pheromone samples were obtained both by excision of the pheromone glands and by airborne trapping of released volatiles. In the former method of sample preparation the sexually mature males were anesthetized with $CO_2$, submerged under tap water, then the III-IV dorsal abdominal glands were dissected from the insects, dried, and extracted with either carbon disulfide or methylene chloride. For airborne trapping of the pheromone, single adult males were contained in an all glass closed system and air was drawn by vacuum at 65 ml/min over the insect and through a few mg of an activated carbon filter (Ambersorb). The trapped volatiles were then extracted from the filter with 100-200 μl of methylene chloride.

Extracts were examined gas chromatographically on three different columns and instruments. Most of the initial GC work was done with a Micro Tek 160 GC equipped with a flame ionization detector on a 10% SP-1000 AW Chromosorb W (60/120) column programmed from 60° to 195° C. at 5° C./min using nitrogen as the carrier gas. Samples were also examined on a Tracor 222 GC with a flame ionization detector coupled to a Varian CDS 111 automatic peak area integrator, using helium as the carrier gas, and a 3% OV-1 on Chromosorb W (80/100) column programmed from 80° to 205° C. at 5° C./min. Gland extracts and airborne extracts were compared using a Packard 421 GC equipped with a flame ionization detector on a 3% OV-275 AW Chromosorb W (100/120) column programmed from 60° to 210° C. at 10° C./min using nitrogen as the carrier gas.

Individual components of the pheromone were isolated using a Varian 3700 GC equipped with a thermal conductivity detector on a 3% OV-275 AW Chromosorb W (100/120) column programmed from 60° to 160° C. at 10° C./min using helium as the carrier gas. The optically active components were trapped separately as they eluted in glass capillary tubes jacketed in dry ice. Measurements of the optical rotation of isolated components were made in ethanol solutions with a 0.7 ml cell in a Rudolph 70 polarimeter.

The components of the pheromone were identified from their mass spectra obtained with the use of a combined GC-MS system as described in *J. Chem. Ecol.* 4, 161-172, 1978. The mass spectrometer was an LKB-9000 operated at 70 eV, with a source temperature of 270° C., separator at 260° C., and 60 μA ionization current. Separations were achieved using either a 1% SP-1000 column or a 1% OV-17 column, programmed from 50° to 225° C. at 10° C./min. The mass spectra of the first four compounds to elute matched published spectra of (E)-2-hexenal, linalool, benzyl alcohol, and terpinen-4-ol, respectively. The fifth, and major peak in the gland extracts, matched the spectrum of authentic α-terpineol. Standards of these compounds each gave a single peak coincident with the natural product by GC when coinjected with gland extract. A sixth peak, eluting at the tail end of the α-terpineol peak, is identified as cis-piperitol based on m/e fragments at 86, 139, and 154 superimposed on the α-terpineol spectrum.

The optical rotation of 1.393 mg of α-terpineol isolated from extracts of male pheromone glands was calculated to be $[\alpha]_D^{27} = +115°$. The rotation of (+)-α-terpineol $[\alpha]_D^{20} = +100°$ according to J. Colonge and J. Crabalona in the *Bull. Soc. Chim.* France 1959, 1505-1511. These data suggest that the insect produces only the plus enantiomer of α-terpineol, although this method of determination does not exclude the possibility that a small amount of the antipode is also produced by the insect. Too little linalool, terpinen-4-ol, or cis-piperitol was isolated for accurate determinations of optical rotation. However, the rotation of linalool did appear to be positive.

The enantiomers of α-terpineol were synthesized and recrystallized three times by the method of J. Colonge and J. Crabalona in the *Bull. Soc. Chim.* France 1959, 1505-1511. The (+)-α-terpineol obtained had 1.6% of the antipode present, and the (−)-α-terpineol obtained had 1.9% of the antipode present.

Comparison of gas chromatograms of the gland extracts and airborne extracts demonstrated that there were only small differences in the proportions of components for these two types of extracts. Gland extracts from male *P. maculiventris* collected in Missouri, Georgia, New York, and Maryland were compared by GC and there were no obvious differences in composition. In addition, the composition of the secretion was the same for males raised on mealworms as those reared on cabbage worms (*Trichoplusia ni*). The synthetic pheromone was formulated to match the composition of airborne extracts based on the % area of the peaks from GC chromatograms with the exception of cis-piperitol. A formulation of 354 μl (E)-2-hexenal, 216 μl α-terpineol, 19.7 μl benzyl alcohol, 2.4 μl linalool, and 2.0 μl terpinen-4-ol closely approximated the proportion of these components in the natural airborne secretion when examined by GC and these volumes were convenient for preparing the mixture. Expressed in mol %, the proportion of the components in the synthetic pheromone is as follows: (E)-2-hexenal, 67.10; α-terpineol, 28.26; benzyl alcohol, 4.10; linalool, 0.29; terpinen-4-ol, 0.25. Racemic linalool and (+)-terpinen-4-ol were used in the pheromone formulation.

Field tests were conducted in the following manner. Two types of sticky traps were used: Pherocon TM 1 C Traps and 10×20 cm sheet metal plates coated on each side with Tack Trap TM. Other equivalent traps and coating materials may also be used. Test solutions, 10 μl of synthetic pheromone mixture per trap, were placed on rubber septa, 5×9 mm rubber stoppers, sleeve-type, located in the bottom of the traps or suspended inside a hole cut in the middle of the metal plate traps. The traps were hung at shoulder height on tree branches along powerline cuts through woods or along the border of woods with grass fields.

Table 1 gives the trap catches for three months of *P. maculiventris* and its parasitoids in Pherocon traps baited every other day with gland extracts of laboratory reared bugs. Extracts of the presumably defensive metathoracic gland (MTG) and dorsal abdominal glands (DAG) were prepared the morning of rebaiting, and each trap was baited with the appropriate gland(s) extract from a single adult. The male DAG extract was the only treatment in this test that was attractive to *P. maculiventris* and its tachinid fly parasitoids, *Euclytia flava* and *Hemyda aurata*. More female parasitoids were caught than males and more *H. aurata* were caught than *E. flava*. Only one female *P. maculiventris* was caught. Although the total number of insects attracted in this experiment was small, the test does indicate that the male DAG are the source of the aggregation pheromone in *P. maculiventris*.

Two field trapping experiments for the *P. maculiventris* synthetic aggregation pheromone were performed simultaneously. One experiment was designed to compare the attractiveness of blank traps, traps with live males or females, and traps with the synthetic pheromone containing (+)-α-terpineol (plus-pheromone). The second experiment was designed to compare the attractiveness of synthetic pheromone containing (+)-α-terpineol (plus-pheromone) to synthetic pheromone containing (−)-α-terpineol (minus-pheromone). All traps were checked daily, weather permitting. Synthetic pheromone traps were rebaited daily with 10 μl of the neat mixture and the traps containing live insects were reprovisioned with mealworm pupae and water as needed. Many solider bugs were attracted to the vicinity of traps but were not entangled in the traps. These bugs were collected and included with data for bugs caught in the traps, but only those parasitoids entangled in the traps are included in the data tabulated in Tables 2 and 3 which show the total number of bugs attracted to each trap during one entire season, a period of about six months. Live female traps and control traps were completely unattractive, while live male and plus-pheromone traps attracted many of the bugs and its parasitoids (Table 2). Many more of these insects were attracted by the plus-pheromone than by live males. The plus-pheromone traps caught nearly equal numbers of male and female *E. flava*, but a great excess of female *H. aurata* were caught in these traps. In the traps containing live males an excess of female *E. flava* were caught but the excess of female *H. aurata* was not as pronounced. Data for the comparison of the field attractiveness of synthetic pheromone containing either (+)-α-terpineol or (−)-α-terpineol are presented in Table 3. The plus-pheromone was much more attractive to *P. maculiventris* adults and its parasitoids than the minus-pheromone. In fact, the attraction to the minus-pheromone may be entirely due to contamination by the plus enantiomer of α-terpineol. This suggests that (−)-α-terpineol is not inhibitory and therefore it may be possible to use racemic α-terpineol in the pheromone mixture. The data for parasitoid attraction suggest that *H. aurata* are less abundant than *E. flava*, but are more sensitive than *E. flava* to the pheromone of *P. maculiventris*. The spined soldier bug is the only known host of *H. aurata*, whereas *E. flava* has been reared from at least three other species of phytophagous pentatomids. Thus, *H. aurata* is apparently a specific parasitoid and *E. flava* is a nonspecific parasitoid of *P. maculiventris*. The parasitic tachinid fly, *Cylindromyia fumipennis*, reportedly parasitizes at least 10 species of pentatomid bugs, including *P. maculiventris*, in some parts of the U.S.: therefore, it is likely that this species of parasitoid will be attracted to the synthetic pheromone of *P. maculiventris* when tested in those locations. During the peak in the spring population of *E. flava*, it was possible to induce them to parasitize laboratory reared adult males of the foreign pentatomid pest, *Nezara viridula*, by confining these bugs in a cage made of wire mesh large enough to allow *E. flava* to enter and baiting the cage with 10 μl of the *P. maculiventris* plus-pheromone. Finally, the total number of female spined soldier bugs caught was significantly greater than males. This is probably due to greater mortality from parasitization suffered by males.

Although the pheromones of hundreds of species of insect pests have been identified and synthesized, the pheromone of this invention is the first synthetic pheromone of an insect in the order Hemiptera and the first synthetic aggregation pheromone of a beneficial predatory insect.

An inherent difficulty in using the pheromones of pests for their control is that the individuals attracted by the pheromone must then somehow be destroyed. Using pheromones to attract beneficial species does not have this inherent difficulty. In addition, most of the pheromones identified for insect pests release stereotyped behavior only in adults, however, the larval stage of an insect pest usually does the most damage. Control programs involving a pest's pheromone suppress later generations of the pest but do not affect larvae responsible for an ongoing infestation. On the contrary, attraction of a predator will have an immediate impact on the econmically important stage of the pest. Since the geographic range of *P. maculiventris* is large, most of North America, and the insect feeds on a wide variety of prey, over 50 species including many economic pests, the aggregation pheromone of this predator is very practical and can be quite useful. *Podisus maculiventris* has been approved for introduction into Europe for biological control, but attempts to establish this insect in Europe, beginning in the 1930's, have been unsuccessful. The pheromone of this invention can be useful in establishing *P. maculiventris* in Europe and other suitable geographic regions by focusing the insects near the point of release, thereby enhancing their initial reproductive success. It can also be used to attract *P. maculiventris* to pest infested crops, gardens and trees and to hold them in the desired area for biological control of the pests. Another use is to attract *P. maculiventris* out of a pest infested area prior to applying pesticide thereby avoiding destruction of this beneficial predator. The pheromone can also be used to attract *H. aurata, E. flava* and other parasitoids of *P. maculiventris* in order to destroy them and prevent the decimation of the *P. maculiventris* population.

In combination with the synthetic pheromone of this invention, the predaceous nature of the soldier bug, *P. masculiventris*, can be used to manage or eliminate a pest population in a pest infested or other chosen area by luring solider bugs to the area with one or more traps baited with the synthetic pheromone. In lieu of using baited traps, a more ideal way of utilizing the above combination in pest management is to formulate the pheromone in a slow-release preparation. One way of doing this is to formulate the pheromone with a plastic or other suitable solid or semi-solid material from which the pheromone is released at a desired or predetermined rate. The plastic or other material is then pelletized or made into other suitable forms, preferably those forms which provide the largest surface area. The pellets or other forms are then broadcast over the pest infested or chosen area. PVC (polyvinylchloride) is a suitable plastic for this purpose. The PVC is mixed with a plasticizer and the pheromone to produce a plastic semi-solid product which is prepared to contain the desired amount of pheromone up to at least 50% by weight. A procedure for combining the pheromone with PVC is described in Environmental Entomology 2, 607–610, 1973. The synthetic pheromone may also be microencapsulated in biodegradable polymers such as polylactic acid and copolymers of lactic and glycolic acids. These thermoplastic polymers and copolymers degrade to natural materials that are harmless to the environment while they slowly release the pheromone. The encapsulation procedure is known in the art and one such procedure is described in Environmental Sci. Technol. 7, 955–956, 1973. Another procedure is described in U.S. Pat. No. 4,272,398.

In order to introduce solider bugs into a pest-infested area or into a foreign country, they must be trapped in a manner in which they are not harmed. Therefore, I designed a trap for this purpose. The trap does not use any sticky or other material harmful to the bugs. The pheromone is pinned or otherwise attached to the bottom of the trap and the attracted insects enter through a hole in the end of one of the screen cones on the sides of the trap. Once trapped, the bugs cannot escape. The bottom of the trap is easily removed for rebaiting or removing captured insects.

Since *P. maculiventris* produces only (+)-α-terpineol, I used this enantiomer in the synthetic pheromone compositions described heretofore. However, I have found that the commercially available racemic form, (±)-α-terpineol can be used with an insignificant loss of activity. I have also discovered two new synthetic compositions that are simpler and more active than the compositions which contained the components found in the airborne secretions of *P. maculiventris*.

The components of the two compositions expressed as % by volume are as follows:
1. 53.6% (±)-α-terpineol, 43.9% (E)-2-hexenal, and 2.5% benzyl alcohol, and
2. 55% (±)-α-terpineol and 45% (E)-2-hexenal.

The number of *Podisus maculiventris* adults caught alive in traps baited with Compositions 1 and 2 is compared in Table 4 with the number caught by Composition 3 prepared by blending 1739 µl (E)-2-hexenal, 2123 µl (±)-α-terpineol, 96.8 µl benzyl alcohol, 11.8 µl (±)-linalool, 9.8 µl (+)-terpinen-4-ol, and 19.6 µl trans-piperitol.

The total volume was 4 ml. Composition 3 contains the same components that were noted above to be found in the airborne secretions of *P. maculiventris* adult males. However, it contains trans- rather than cis-piperitol because I found that the secretions contain both trans- and cis-piperitol in a ratio of 1.59 to 0.07. The 4 ml of neat blend was mixed with 20 ml of plasticized polyvinyl chloride to make a slow-release pheromone formulation. Composition 1 was formulated by blending the components in the same volume as used in the complete formulation, that is, 2123 µl (±)-α-terpineol, 1739 µl (E)-2-hexenal, and 96.8 µl benzyl alcohol. The total volume, 4 ml minus the total volume of the omitted trans-piperitol, (±)-terpinen-4-ol, and (±)-linalool in Composition 3, was mixed with 20 ml plasticized polyvinyl chloride to make a slow-release formulation. Composition 2 was formulated by blending the components in the same volume as used in Composition 3 and the total volume adjusted as in Composition 1. The resulting volume of neat mixture was mixed with 20 ml plasticized polyvinyl chloride to make a slow-release formulation. The (±)-α-terpineol alone and the (E)-2-hexenal alone were prepared and made into a slow-release formulation in the same manner as Compositions 1 and 2. The number of *P. maculiventris* adults caught by a blank control and by (±)-α-terpineol above and by (E)-2-hexenal above is also shown. The results in Table 4 show that Compositions 1 and 2 provide more attractancy than Composition 3. In fact, Composition 1 exhibits far more attractancy for *P. maculiventris* than does Composition 3. It is interesting to note that while Composition 2 provides more attractancy than Composition 3, each of its components when tested alone provides no or negligible attractancy.

Composition 4, containing the same components in the same volumes as in Composition 3 with the exception of linalool and with the total volume adjusted to 4 ml minus the volume of the omitted linalool exhibits a significant increase in attractancy over that of Composition 3.

Composition 4 contains by volume, 43.6% (E)-2-hexenal, 53.2% (±)-α-terpineol, 2.4% benzyl alcohol, 0.25% (+)-terpinen-4-ol, and 0.49% trans-piperitol.

TABLE 1

| extract | P. maculiventris | | E. flava | | H. aurata | |
|---|---|---|---|---|---|---|
| | ♂ | ♀ | ♂ | ♀ | ♂ | ♀ |
| control | 0 | 0 | 0 | 0 | 1 | 2 |
| MTG | 0 | 0 | 0 | 0 | 0 | 0 |
| ♀DAG | 0 | 0 | 0 | 0 | 0 | 0 |
| ♂DAG | 0 | 1 | 0 | 5 | 2 | 17 |
| DAG + MTG | 0 | 0 | 0 | 0 | 0 | 0 |

DAG = dorsal abdominal glands
MTG = metathoracic glands

TABLE 2

| lure | P. maculiventris | | E. flava | | H. aurata | |
|---|---|---|---|---|---|---|
| | ♂ | ♀ | ♂ | ♀ | ♂ | ♀ |
| control | 0 | 0 | 0 | 0 | 0 | 0 |
| live ♀ | 0 | 0 | 0 | 0 | 0 | 0 |
| live ♂ | 30 | 25 | 15 | 104 | 5 | 26 |
| plus-pheromone | 147 | 164 | 863 | 907 | 22 | 235 |

TABLE 3

| lure | P. maculiventris | | E. flava | | H. aurata | |
|---|---|---|---|---|---|---|
| | ♂ | ♀ | ♂ | ♀ | ♂ | ♀ |
| plus-pheromone | 433 | 504 | 2473 | 2463 | 27 | 637 |
| minus-pheromone | 56 | 57 | 83 | 189 | 9 | 439 |

TABLE 4

| Pheromone Composition | P. Maculiventris Trapped |
|---|---|
| Composition 1 | 253 |
| Composition 2 | 174 |
| Composition 3 | 151 |
| Composition 4 | 219 |
| (±)-α-terpineol | 4 |
| (E)-2-hexenal | 0 |
| Blank control | 0 |

I claim:

1. A synthetic pheromone composition for attracting the spined soldier bug, *Podisus maculiventris* consisting of an effective attractant mixture of, by volume, 53.6% (±)-α-terpineol; 43.9% (E)-2-hexenal; and 2.5% benzyl alcohol.

2. A synthetic pheromone composition for attracting the spined soldier bug, *Podisus maculiventris*, consisting of an effective attractant mixture of, by volume, 55% (±)-α-terpineol and 45% (E)-2-hexenal.

3. A synthetic pheromone composition for attracting the spined soldier bug, *Podisus maculiventris*, consisting of an effective attractant mixture of, by volume, 43.6% (E)-2-hexenal; 53.2% (±)-α-terpineol; 2.4% benzyl alcohol; 0.25% (+)-terpinen-4-ol; and 0.49% trans piperitol.

4. A method of attracting the spined soldier bug, *Podisus maculiventris* to a desired area, comprising distributing in said area an effective attractant mixture of, by volume, 53.6% (±)-α-terpineol, 43.9% (E)-2-hexenal, and 2.5% benzyl alcohol.

5. A method of attracting the spined soldier bug, *Podisus maculiventris* to a desired area, comprising distributing in said area an effective attractant mixture of, by volume, 55% (±)-α-terpineol and 45% (E)-2-hexenal.

6. A method of attracting the spined soldier bug, *Podisus maculiventris* to a desired area, comprising distributing in said area an effective attractant mixture of, by volume, 43.6% (E)-2-hexenal, 53.2% (±)-α-terpineol, 2.4% benzyl alcohol, 0.25% (+)-terpinen-4-ol, and 0.49% trans-piperitol.

* * * * *